(12) United States Patent
Olafsdottir et al.

(10) Patent No.: US 6,319,710 B1
(45) Date of Patent: Nov. 20, 2001

(54) HUMAN NARCOLEPSY GENE

(75) Inventors: Berglind Ran Olafsdottir, Reykjavik (IS); Jeffrey Gulcher, Chicago, IL (US)

(73) Assignee: deCODE genetics ehf., Reykjavik (IS)

( * ) Notice: Subject to any disclaimer, the term of this patent is extended or adjusted under 35 U.S.C. 154(b) by 0 days.

(21) Appl. No.: 09/479,128

(22) Filed: Jan. 7, 2000

Related U.S. Application Data

(63) Continuation-in-part of application No. 09/379,083, filed on Aug. 23, 1999, now abandoned.

(51) Int. Cl.$^7$ .............................. C12N 5/10; C12N 15/12; C12N 15/63; C07H 21/04
(52) U.S. Cl. ...................... 435/325; 435/320.1; 435/455; 536/23.1; 536/23.5
(58) Field of Search .............................. 435/6, 69.1, 70.1, 435/320.1, 325, 455; 514/44; 536/23.1, 23.5

(56) References Cited

FOREIGN PATENT DOCUMENTS

| 0875566A2 | 11/1998 | (EP) . |
| WO 96/34877 | 11/1996 | (WO) . |

OTHER PUBLICATIONS

Peyron, Christelle, et al., "A mutation in a case of early onset narcolepsy and a generalized absence of hypocretin peptides in human narcoleptic brains", *Nature Medicine*, vol. 6, No. 9, pp. 991–997 Sep. 2000).
Pavitt, R., "Human DNA sequence from clone RP11–73M7" GenBank Accession No. AL355514 (May 7, 2000).
Aldrich, et al., "Narcolepsy and the *Hypocretin Receptor 2* Gene" *Neuron*, vol. 23, pp. 625–626 (Aug. 1999).
Verma et al., Nature, 387:239–242, 1997.*
Orkin et al., in "Report and Recommendations of the Panel to Assess the NIH Investment in Research on Gene Therapy", Dec. 7, 1995.*
Sakurai, T., et al., "Structure and Function of Human Prepo–orexin Gene," *J. of Biol. Chem.* 274(25) :17771–17776 (1999).

Lin, L., et al., "The Sleep Disorder Canine Narcolepsy is Caused by a Mutation in the *Hypocretin (Orexin) Receptor 2* Gene," *Cell* 98:365–376 (1999).
Chemelli, R.M., et al., "Narcolepsy in *orexin* Knockout Mice: Molecular Genetics of Sleep Regulation,"*Cell* 98:437–451 (1999).
Siegel, J.M., "Narcolepsy: A Key Role for Hypocretins (*Orexins*)," *Cell* 98:409–412 (1999).
Sakurai, T., et al., "Orexins and Orexin Receptors: A Family of Hypothalamic Neuropeptides and G Protein–Coupled Receptors that Regulate Feeding Behavior,"*Cell* 92:573–585 (1998).
De Lecea, L., et al., "The hypocretins: Hypothalamus–specific peptides with neuroexcitatory activity," *Proc. Natl. Acad. Sci USA* 95:322–327 (1998).
Mignot, E., et al., "Narcolepsy and immunity," *Adv. in Neuroimmunology* 5:23–37 (1995).
Mignot, E., "Genetic and familial aspects of narcolepsy," *Neuro 50*(Suppl 1) :S16–S22 (1998).
Faraco, J., et al., "Genetic Studies in Narcolepsy, a Disorder Affecting REM Sleep," *Amer. Genet. Assoc.* 90:129–132 (1997).
Kadotani, H., et al., "Genetic Studies in the Sleep Disorder Narcolepsy," *Genome Res.* 8:427–434 (1998).
Mayer, G., et al., "Segregation of HLA genes in multicase narcolepsy families," *J. Sleep Res.* 7:127–133 (1998).
Nishino, S., et al., "Hypocretin (Orexin) Deficiency in Human Narcolepsy," *Lancet* 355(9197):39–40 (2000).
Taheri, S., et al., "Role of Orexins in Sleep and Arousal Mechanisms," *Lancet* 355(9206):847 (2000).

* cited by examiner

Primary Examiner—Deborah J. R. Clark
Assistant Examiner—Janet M. Kerr
(74) Attorney, Agent, or Firm—Hamilton, Brook, Smith and Reynolds, P.C.

(57) ABSTRACT

The gene for hypocretin (orexin) receptor 1 (HCRTR1), which is associated with narcolepsy, is disclosed. Also described are methods of diagnosis of narcolepsy, pharmaceutical compositions comprising nucleic acids comprising the HCRTR1 gene, as well as methods of therapy of narcolepsy.

3 Claims, 5 Drawing Sheets

```
LOCUS                        9785 bp   DNA        PRI      12-NOV-1999
DEFINITION   Human hypocretin (orexin) receptor 1 (HCRTR1) gene, complete cds,complete sequence.
ACCESSION
NID
VERSION
KEYWORDS
SOURCE       human.
  ORGANISM   Homo sapiens
             Eukaryota; Metazoa; Chordata; Craniata; Vertebrata; Mammalia;
             Eutheria; Primates; Catarrhini; Hominidae; Homo.
REFERENCE    1 (bases 1-9785)
AUTHORS
  TITLE      Direct Submission
  JOURNAL         Submitted (_____) deCode Genetics, Inc., Lynghals 1,
             IS-110 Reykjavik, Iceland.
FEATURES             Location/Qualifiers
     source          1..9785
                     /organism="Homo sapiens"
                     /db_xref="taxon : 9606"
                     /chromosome="1"
                     /map="1p33"
                     /clone="BAC 333N1"
     gene            1117..9190
                     /gene="HCRTR1"
                     /note="OX1R"
                     /db_xref="LocusID:3061"
                     /db_xref="MIM:602392"
     exon            1117..1468
                     /gene="HCRTR1"
                     /number=1
     CDS             join(1270..1468, 1609..1787, 2920..3163, 3554..3669, 5599..5825, 7074..7195,
                     8867..9190)
                     /gene="HCRTR1"
                     /note="HCRTR1 exons defined by comparison to mRNA sequence (NM_001525)"
                     /codon_start=1
                     /product="HCRTR1/orexin receptor 1"
                     /db_xref="LocusID:3061"
                     /db_xref="MIM:602392"
                     /protein_id="NP_001516.1"
                     /db_xref="PID:g4557637"
                     /db_xref="GI:4557637"
                     /translation="MEPSATPGAQMGVPPGSREPSPVPPDYEDEFLRYLWRDYLYPKQ
                     YEWVLIAAYVAVFVVALVGNTLVCLAVWRNHHMRTVTNYFIVNLSLADVLVTAICLPA
                     SLLVDITESWLFGHALCKVIPYLQAVSVSVAVLTLSFIALDRWYAICHPLLFKSTARR
                     ARGSILGIWAVSLAIMVPQAAVMECSSVLPELANRTRLFSVCDERWADDLYPKIYHSC
                     FFIVTYLAPLGLMAMAYFQIFRKLWGRQIPGTTSALVRNWKRPSDQLGDLEQGLSGEP
                     QPRARAFLAEVKQMRARRKTAKMLMVVLLVFALCYLPISVLNVLKRVFGMFRQASDRE
                     AVYYACFTFSHWLVYANSAANPIIYNFLSGKFREQFKAAFSCCLPGLGPCGSLKAPSPR
                     SSASHKSLSLQSRCSISKISEHVVLTSVTTVLP
     exon            1609..1787
                     /gene="HCRTR1"
                     /number=2
```

FIG. 1A

| | |
|---|---|
| exon | 2920..3163<br>/gene="HCRTR1"<br>/number=3 |
| exon | 3554..3669<br>/gene="HCRTR1"<br>/number=4 |
| exon | 5599..5825<br>/gene="HCRTR1"<br>/number=5 |
| exon | 7074..7195<br>/gene="HCRTR1"<br>/number=6 |
| exon | 8867..9190<br>/gene="HCRTR1"<br>/number=7 |

BASE COUNT   2212 a   2759 c   2685 g   2129 t

```
AAAGGACCCGCGGCGAGGGATGGGAGGAGCCAAGAGTCTCGGGGGGTAACCTGGGTGCTG
GGAGACTGGCTCCTCGGCCAGCGCTGCTCTCCTCTAGGCAGGCTCCGAGTGCCCTCGCTC
CCCCGCGCCTTCCCGGAGCCCCGCCAGCCCCCGAGGTGCAGGAAGGTCCCGCGGACGGAG
CGGGCCTGCCGGCGTTCAGTGGGGTATGAAGGCGTCCCCTCCCCTTCCCCAGGGGTCTCC
AGGGATCCGCAACCCTCCGGCACCTGGCCGGGGTCGTCCTAGCCCAGCCGGGGGAAGGAG
GGGCTGAGTGCGGGAGGAGGGGAGGGGCGGGGAGCTGGGCTGGCTGGATTTATGAATGGA
GAGCGACCCGCGCGCCGGAACAGCGGCTCCTGGCGGCCGTCGGGGAGCGTCGCGGCCCTG
GGGACCCAAAGGGGCCTCTTAGGGGGCCTGGATGCTCCCCTTGCTCGCAAGGGGTCGTCA
GTCCCTCCGCGCACCACCCCCACTGTGTGTGTGTTGTATGTGTGCGTGTCCGCGAGTGCC
CACCGGAGGGTCTGGCAGGTATGGCGGGTGGGGCTTGGGTCTCTAACACCTCCCTTGGCC
CGTTTTCCCAACCCAAAGTTAAAGCCTCTGAACTGGCTCAAGAAATATTTGCAATCGGGA
TGGCTTCTCCTCCCAAATCTACGGTGTTTGGTGGGTTCGAACAGACCTGGCTTAAGAGCT
TTGTGACCTTGAGCAAGAGACTCAATCTCTCTGAGCTTCGGTCTCATCTGCAAAGCAGGG
TACCCTAATAATGGTAACCGGAAACGTCCCCGAAACTACCTTCTCGTACCAGGTTCTTGG
TGAAGCACTTGGCACGCATCGGAGCTCATTACTCCTCATCGTGGTCCTGTAAGGTATGTA
GGGCTGTCACCCCATTAGACAGATGGGGAAACCAAGGCTGAAAGAGGCCAGGTAAGCTAC
CCAAGGCAACTGGTGTGGAATTGGGATGCAACCCAGGTCTGTCTTCCTCCACCAATTTCA
TGACTGTGAGAATTAAGAGGGAACTTATACGCAAAGCGCCTGGCACAATCCCTAATGTTT
CCTTCCTTCTCTCTTTTCCCACTCCCTCCTTTCCTTCCTCCCTTCAGGAAGTTTGAGGCT
GAGACCCGAAAAGACCTGGGTGCAAGCCTCCAGGCACCCTGAAGGGAGTGGGCTGAGGGC
TGGCCCAAGCTCCCTCCTCTCCCTCTGTAGAGCCTAGGATGCCCCTCTGCTGCAGCGGCT
CCTGAGCTCATGGAGCCCTCAGCCACCCCAGGGGCCCAGATGGGGGTCCCCCCTGGCAGC
AGAGAGCCGTCCCCTGTGCCTCCAGACTATGAAGATGAGTTTCTCCGCTATCTGTGGCGC
GATTATCTGTACCCAAAACAGTATGAGTGGGTCCTCATCGCAGCCTATGTGGCTGTGTTC
GTCGTGGCCCTGGTGGGCAACACGCTGGGTAGGTCCAGGGCTTGCCCGGCAGTGCTGCCG
GCTTTCCCTGGGGATTGAAGGGGGTTGTGTGGGAGGAGGGCTCGCTGATTAGGCAGAACT
AGGATGGGTGTGGCTCTGCCACCAGCTTCACCTCGCTGCACCCTGCAGTCTGCCTGGCCG
TGTGGCGGAACCACCACATGAGGACAGTCACCAACTACTTCATTGTCAACCTGTCCCTGG
CTGACGTTCTGGTGACTGCTATCTGCCTGCCGGCCAGCCTGCTGGTGGACATCACTGAGT
CCTGGCTGTTCGGCCATGCCCTCTGCAAGGTCATCCCCTATCTACAGGTGAGCTCTGCCC
AGGCACCCCTCACCACTCCTTGTCACGCCTGTAAAAAACCCACGGCCTTGCATAGGTCTC
AGTGACCCCCAGACTTGCCTTTCAGACAGGTCAGTGGCTCATGACCCCTGAAGTGTCATC
CTCTGCTGCTAGCAAGGGCAAGCCACCAGATCAGACACTCGAGGACACAGACACAACCCC
ACACACTCACAGAGATCCCCTCCTGGTCACAGCCACAGACATATACATAGACACGTGTGG
ACATGTATAGTCACCTCCAGGTACACAGGCACACAGTCAAGGAGAGAGGCAACAGCCCAC
AGTGACACATACACGACACCCTAGGCCTGCTCCCCAATCCCAAAGGGGCAGACGTGAGGG
GCCTGATGGAAACAGCCGTCTCCTCTCCCTCCTGCACTGGCCAGGAAAGACCCCAGTGGT
```

FIG. 1B

```
GGAAACCAGGATGTCCGGATGGGGTTAGTGGGGTGGAAGGAAGGCTTCTCTCAGTTTGTA
TCCTGTGATCCACTTCCTGCACCCCAGAGGGCAGGGGCACCCCTAGAGGCAATGCCCAC
ACACCTCTGACCCAGACTCATCTCTGCCTCCCAGAATGAGGGCTTTTTCCTAACAGCCTG
GGGAAGGGATGGCATTCCATGGCAGAGATAAATGCCTCTTGGATTTCCCACTATTTTGAG
GCTCCCCACTCAACTGGTTAACTCTGGTGACCCTGAGCATAAAGACAGATGGATGAGGGA
ATTCTGTGCCTCAGTTTCCTCATCTGTAACAGGGGGCAAGAGCGCTTTGTGGGATTGTC
ATGAGGATGATGAGAACAGTGCCCAGCACATAGTAAGTTACGTAGGTGCAAGTTATTATT
CACCGGAGGGGTGCACCTACCATGTGCCAGGTCTAAAGCTGGACATTGTTTGTACATGAT
TTCACTTATTCGCACAAGAATCTTGCCAGGTAGATGGTATATTCCCATTCTGTAGACGAG
GCTCAGAGAGGGTGAGTGACTTGCCCACATTTACACAGCCAGTAAGTGGTGGAGTCAGGA
TTTGCACTGCCCTGCACCTGCCGTCAGCCTCCTCACTCACCTACTCTCACATCGCTGGGT
GGCCCCCAAAATGACCGACGTTGTGTCCCCGTGGGGCAGGCTGTGTCCGTGTCAGTGGCA
GTGCTAACTCTCAGCTTCATCGCCCTGGACCGCTGGTATGCCATCTGCCACCCACTATTG
TTCAAGAGCACAGCCCGGCGGGCCCGTGGCTCCATCCTGGGCATCTGGGCTGTGTCGCTG
GCCATCATGGTGCCCCAGGCTGCAGTCATGGAATGCAGCAGTGTGCTGCCTGAGCTAGCC
AACCGCACACGGCTCTTCTCAGTCTGTGATGAACGCTGGGCAGGTAATGGTGGAAGCCTC
AAGCAGGCATCCCCTCAGGTGGGCACTTTGGGAGCACGTACCCCTAGGACAGGCATCTAG
CAGGGTCCCTTCCAAAGTGGGAAATCCCAGAGCAGGTATTTCCCTAGGGGACACCCTAGA
CTGGCTCCTACCAGGGATACTCCCAGGGTGGGTGCCTCCCCTCATGTAGACATCTGCTCT
AGTGTAGATGTCCTTCCAGGAGGGACAACCCAAGTTGGACAACTCCAGGGTCTCTGTCTG
TCATGGTGGCTGTATGGGGTCCAGCTGCTCCTAGGCCTTGCTTTGGCCGTAGTCAGGACA
GGGTGGCATTGCTAACCAGGGCAGGGTGGGGCTCACGGATTGGGCCTGACTCTGCATCTC
TTGACCCCTGCAGATGACCTCTATCCCAAGATCTACCACAGTTGCTTCTTTATTGTCACC
TACCTGGCCCCACTGGGCCTCATGGCCATGGCCTATTTCCAGATATTCCGCAAGCTCTGG
GGCCGCCAGGTGAGGCCCACTCTGGGCAGGGGCTAGGCCAGTCACTGTGTGGGCTGGGGG
TGGGAGGGCTACTGGTCTAACTGAGTAGGCAGTCCTCTGCCATCAGCACATGCCATCTTG
GCTGCAACCAAAGAGAGGGGAAGCCCAGAGACACGTCAAACTCAAGGCCAAAAGCACCAG
TGGCTACCCTGGAATGGAATAGTAACACGTCCTTCTATTAGTGGTTGGCGTTTATTGAAG
TATCCACTCCCAGATAATCTTGCATCCTCTTAGCCACCATATATTACCCACATTAAATAT
ATGAGAAAACCGAGACCCAGAAGATCAACATAACTTCCCCCAAACCACTCAGCTAGTGAG
TAGATCAGGAACTAAAGCCCAGATCTGTGAGCTCCCACTGCTCAGTTTAGTACCACTGCA
ACAATAATAATAGCAACTCCGTGGTGCTTGCCAAATTAGGCACTTTGCATCCAATGTCTT
AACAACTATCTAACAAAAGAAGCAACATTACCCACGTCACAAATGCCAAATAAGGGCAAC
CAACTTGCCAGATTCAACAGCAGCAGAGCCTTCTGGTTCCAGGGCCTGTCTTCTTTCCTG
CATTACAGACTGACCCACGGTGGGTTCTTAGGTTTTTGGGGGCAGGGGTGGTCAGAGG
CCCTTGGCCTAGCGAGTGGGAGTCCTGGATTGGCGTCTGGGCGGTGAGAAAGGCAGGCC
AGAACATGACCAGGCTCAGGAAGGGACTCTCACACTTGGGGATGTCACCTACATTCCACA
GGAAGTACTGGCTTGCACCCAGGCCATGCCGGGCAGCGGATGGGACACGGACTGGCTGT
GACCCAGGTCCTGCCTTGGAGGAGCACCCAGTCCAGTAGGACCCTTCCTGACTGGCCAGC
CCTGTAGTCCACCAACACTCATCATCTGCTCCCCACAGACCCCCCAGCCAAGCAGGACAC
AGGCACGATCCTCCTCATTTGACAGATATGAAAGCAAGGCTTAGAAAGGAAAATGAGGTG
GCTAAGGTCACATAGCTCACGAATGGCTGAGCTGGCTCTAGACCCGCGTTTCCAGAACTC
CAGCCCCATGCCCCTCTGTGGTGGGTGATTTGAGTGTCCGGTGGCAGGAGAGGCTTCTCC
AGGAGCCCAGAACCACCCCAGGCTTATGGGCACTGGCCCAGGCCATTCGATGCTGCCCAC
CTGCTCACCCCTTGCCCAGGCCTCCTCATAGTCTGGTATGATCCAGGGGAGGCACAACTC
ACCCCCACCCCTACCCTCAAAGATAGTGTTGGAGATTTAGGGAGGATGGATGGGCAGTTG
ACAGGATGTGGCCTGGGGTCTTGTCAAGGTTCCCCACCTCTTTGAGTCTTAGTTGCCTCA
TCTATACCTAAGGACCAATAATATCTTTCCACAAGGCGTGTTGTAGAGGGTTTCACAAAG
AGCTAATGGAAAATGAAAGTCTAGGCTGGGCGCAGTGGCTCACACCTGTATTCCCAGCAC
TTTGGGAGGCTGAGGCAGGCGGATCACCTAAGGTCAGGAGTTCAAGACCAGCCTGGCCAA
CGTGGTGAAACCCCATCTCTACTAAAAATACAAAACTTAGCCCGGTGTGGTGGCGCACAC
CTGTAATCCCAGCTACTCGGGAGGCGAGATTGAAGAGAGCCAAGATTGCACCATTGCACT
CCAGCTTAGGTGACAAGAGTGAAATGCCATCTCAAAAAAAAAAAAAAGAAAAGAAAAGA
AAATGAAAGTCTATCGTTCACTCTCAAGTCCAGAGTGTTAGTCTATCATAAACATTAGAT
TCCTTCCTCTTGCAAGGGTTTTATCCTTTTGCCCATCTCCACCCTGCCCGGGGTCCAGCC
```

FIG. 1C

```
TGGAGTAGGCCCCACAAAAGGCAACCACCCTCCCAAGGTGCTGTACCCACCACTGCTGTC
TCTATGTGTGCTGGACAGATCCCCGGCACCACCTCAGCACTGGTGCGGAACTGGAAGCGC
CCCTCAGACCAGCTGGGGGACCTGGAGCAGGGCCTGAGTGGAGAGCCCCAGCCCCGGGCC
CGCGCCTTCCTGGCTGAAGTGAAGCAGATGCGTGCACGGAGGAAGACAGCCAAGATGCTG
ATGGTGGTGCTGCTGGTCTTCGCCCTCTGCTACCTGCCCATCAGCGTCCTCAATGTCCTT
AAGAGGTGAGAGCACGGGGTATGGTTGGGGTGGGGAGAAGTTTGAGGTTGGGGAAGGAGC
TCTCCTTGCTTGGGAGAAAGACCTGGCTCCACCCCTTCTCCACTATGTGATCTTGGGCAG
GCCATTTCTCTTCTCTGAGCCTCCATCTCCTAGGGCTATCGTGAAAATTCACGCATTCAT
TCACTTAATCATCACATTTTAGGGGGCTGGAAATACAATGAACAAGTGCATAAGACAGAC
AAAGTCCCTGCCTTCATGGAGGCTGCATTCTAGCAGGAGAGAAGGGAAGTAAATAGAAGA
ATCAATGTATATTATAATGTCAGGCAGTGATAACTGCTGGGAAGAAAAATAAAATAGGAC
AGAGAGTGACAATGATAAGGGTTGGTGGGTTTTTGCTTTTGCTTTAGATACAATGGTTTA
AAAAAAGCAGGGGGCCGGGTGCAGTGGCTCACATCTGTAATCCCAACACGTTGGGAGGCC
AAGGAGGGAGGATCGCTTGAGGCCAGGAGTTCAAGATCAGCCCGGGCAACATAATGAGAC
TTCGTCTCTACTAAAATTCAAAAAATTAGCCAGCCATGGTGGCATGTGCCTGTAGTTCTA
GCTACACAGACTGAGGTGGAAGAATAGCTTGAGCCCAGGAGGTTGAGGCTGCAGCGAACC
ATGATTGCACCACTGCACTCCAGCCTGGGTGACACAGCTGTCTCAAAAAAAAAAAAAAAA
AAAAAAAAGCCTTTCCAAGGAAATGACATTTGAGCAGAGACTTGAAGGAAGTGAGAGAGC
TAACCATGCACGTGTCTGTAGGGACAGCCAAAGAGGGTCGCAGGGCGCTGGGGAGAGAAT
GCAGGCTATTGGACAGAAGACAGTTTCACTTTGAGATTGTGCTTGGCCACTTCCTGGTTG
TGTGATCTTCGGCATGTCACTTTACTTCTCTGAGCCTCAGTTTCCTTAATGGAAAAATGG
ATGATGTCTATGATTCATCATGTTGCTGTGAGGATGGATGAGAAAGTGGATGGGAAGCCC
CAGGGGATCCGATGGCCAGGAGGCTAGAGATGCCCATCACGGTGCTTGATACCCTCCATG
CTTGAGAACCCCAAACCCTGGCCAAGACCTCAGGTACAGAAGGCCAGGAAACGTGGACAG
AAGTGGGCAGTAGGAACTCTTGCACTTTACAGCTCAGGTTCTGTGAGCAGCACTCCCCCA
GTACATGCATACGCAGCTACCCCATTTCTGACGCTCCTCCACCCTGGGCCTAGGGTGTTC
GGGATGTTCCGCCAAGCCAGTGACCGCGAAGCTGTCTACGCCTGCTTCACCTTCTCCCAC
TGGCTGGTGTACGCCAACAGCGCTGCCAACCCCATCATCTACAACTTCCTCAGTGGTGAG
CAGGCTGGGGATGCAAAATGACTGAGGGTGGCCAACAGTCCACATGACAAGTCTCCCCAT
CCCCAAGCCAGGGCCCAAATAAAGGATGGTGGGTGAGGATGTACCTGCTGTGGGCACAGT
GATCCTGCTCTGGGAGGACCCACCCCAAGCGGCCCTGGCCTGAGTGGGAGACGGGCCACA
CTCCCTACAGTGGCTGGCACCCAGGATCCAGTTTTGCAGATTCTGCAGACCAGTGAGTGA
GTGGAAGGGCAGGGGCTAGGCCAGCTCACCCCCAACTCCCACCCTGGGTGCAGGCACAGC
AAGACCTCCAATCAGCTCAGGCAGAGGAGTCCATCCTCCCCGGAGGGAGTCAGACCTGTG
GGAGGAGGGCCCTGGAGCCCCTGCCCGAGGAAGGATTGCACAGTCCAGGTGTCAGGGCTA
AAGTAGGGTCACTCTGAGAGACAAGCCAGGCCCAGGGAAGGGCTTCGCCGGCTCAGCTAG
ACACACTGGCAGAGTGACCGGAATCTCAGGGGTTGTCCCCTCTGGAAGTCTTCCTCCCCT
GCCACCCCACTCCCACTCCAGGCCTCTCCTCTCTGCTGTCCCACAGTGCCCACCCCCTC
CCTCTACCTCCCAGTCTCAGGGTGGTAATGGCTCTGAGGCTGAGCTCAGCAGAAGTCTGA
CTCACCAGCCCTCTGACTTTGGGAATAGACTTCTAAAGAACAGGTCCAGATGACTGTTGA
AGCCTGGACAGAAATAATCTTTGAGGAACTATTAAAAGGTTAAAGAAAGGATCAGGAGTC
AATAGTATAACCCTCATTGAGACTCAAGAATTACTCAACAAGGCTGGCTGCGGGTTTCCA
GGTCAGAAAAGAGAATAGATGATGAGCTGTGTGGGGAGGGGAGGGCAGACAGACTTACTG
ACACATATGCCTTTGTTTGGCCTATGTTTACTGAGCACCTACTATGTGCTTGACCCTGTG
CTGGGCACCAGAGAGGCTGGCAGCCTAATGACACATGATCAAAGGGGCTTCAGCCTGACA
AAATCTGTTTCCCTGGTATACTTGGGCTGAATAATGTGGTGTGGTGGTCCCTCCTTCCCT
CCTCCCCCTTGAGAAGGGCTTTGGAATTAGAATTGGGTTCAGCTTCTGGCTGGGTGGACT
TGGGCAAGCCACTGTACCTCTGTGCATCTCATCTGTGAAGTGAGGATAAAGGACTCCAGC
CTTTCAGGGTGCTGGGATGCTCTGGCGGACAGAGGCTGAGGCGCCCAGCACAGCGTGACT
GCCAAATGCAAAAGGGCTGCTGCTGCCGTCATTTTCATCATCAAAGGGCAGAGAGGACAC
AAGCCTCGCAACAGATAGTGACCCCCACGTACACACCAAGGAGAGCAGAGGTGACCTGAG
GCCCCGAGCCAGACACCACGTTTTGAGTCAGCCTCCGAGCCAGAGCACAGTCAAGGAAT
CAGATGGCAATTGCGTCTCTCCTTGGGAACCCGCTCCAGGGCTTCTGTCCTCTCTCTCTG
GCGGTGCCGAGGTTGCCTCAGGGCTCTCCCTCCCAGCTCTATCCCTCCCTCCCTCCCCGC
CCCCTCATAGGCAGCTTGGCTGGAGCTGCGTGGGTGTCCCTGGGCTCAAGGCCCCTTCCT
```

FIG. 1D

```
GCTGCATCTGTCTCCTTATGGCTGTGTCTTTTGTCTCCCAACCAAGGCAAATTCCGGGAG
CAGTTTAAGGCTGCCTTCTCCTGCTGCCTGCCTGGCCTGGGTCCCTGCGGCTCTCTGAAG
GCCCCTAGTCCCCGCTCCTCTGCCAGCCACAAGTCCTTGTCCTTGCAGAGCCGATGCTCC
ATCTCCAAAATCTCTGAGCATGTGGTGCTCACCAGCGTCACCACAGTGCTGCCCTGAGCG
AGGGCTGCCCTGGAGGCTCCGGCTCGGGGATCTGCCCCTACCCCTCATGGAAAGACAGC
TGGATGTGGTGAAAGGCTGTGGCTTCAGTCCTGGGTTTCTGCCTGTGTGACTCTGGATAA
GTCACTTCCTCTGTCTGAGCTTGTGTCCCCTAAGCAGGGTTGATGTGAGGATTAAGCATG
CTGAAGCAAGTGGAAAGCTCCTTGTAAACTGTGAAGTGTTGTGGACATGATTATTGTTGT
ACTTCTCTCATTTGGCCATACCCCACAGTATAATCTGTCCCCATCCTCCTTCCAGAGCTT
GGTCATCCTCCTAAAGACCCCTTTCCTACCCAATTACAGGCCTTCCCTGGAGTCTGCTCT
AAAGGTCCCAACAGGCATTTCCATCTTGTTCCATGGCTCCCTGAAGCCCAGGGCTGCACT
TGGCCAGCTGTTCTGATGCCTGTGTGAACTAATCTGGGCCCAGCCTTTCTCCAGCGGGCC
ACGAGCACAGCCCCACCCTAACCAGGTGCCAAGGGCACACACCACAGACCCGACCTTGTT
GGCTTTGTGGTGTGATAAAACACTCTCCATGGCCACTTGGCAGAGAGGCCAGCAGCCCGA
AGCAACTGTAATTAAAAGCCTGGCACTGAATGTTCCCTTTCCTTGTCATTGCACAAAATC
TGTGCTGCTTAGGTTAGGAGCAGAAGAAGGTGGGGAAGCTGGGGGAGGGAAGACAAGAA
GGCAC
```

FIG. 1E

SEQUENCE LISTING

```
<160> NUMBER OF SEQ ID NOS:  22

<210> SEQ ID NO 1
<211> LENGTH: 9785
<212> TYPE: DNA
<213> ORGANISM: Homo Sapiens
<220> FEATURE:
<221> NAME/KEY: CDS
<222> LOCATION: (1270)...(1468)
```

```
<221> NAME/KEY: CDS
<222> LOCATION: (1609)...(1787)
<221> NAME/KEY: CDS
<222> LOCATION: (2920)...(3163)
<221> NAME/KEY: CDS
<222> LOCATION: (3554)...(3669)
<221> NAME/KEY: CDS
<222> LOCATION: (5599)...(5825)
<221> NAME/KEY: CDS
<222> LOCATION: (7074)...(7195)
<221> NAME/KEY: CDS
<222> LOCATION: (8867)...(9057)

<400> SEQUENCE: 1
```

| | | |
|---|---|---|
| aaaggacccg cggcgaggga tgggaggagc caagagtctc gggggtaac ctgggtgctg | 60 |
| ggagactggc tcctcggcca cgctgctct cctctaggca ggctccgagt gccctcgctc | 120 |
| ccccgcgcct tcccggagcc ccgccagccc ccgaggtgca ggaaggtccc gcggacggag | 180 |
| cgggcctgcc ggcgttcagt gggtatgaa ggcgtcccct cccttcccc aggggtctcc | 240 |
| agggatccgc aaccctccgg cacctggccg gggtcgtcct agcccagccg gggaaggag | 300 |
| gggctgagtg cgggaggagg ggaggggcgg ggagctgggc tggctggatt tatgaatgga | 360 |
| gagcgacccg cgcgccggaa cagcggctcc tggcggccgt cggggagcgt cgcggccctg | 420 |
| gggacccaaa ggggcctctt aggggcctg atgctcccc ttgctcgcaa ggggtcgtca | 480 |
| gtccctccgc gcaccacccc cactgtgtgt gtgttgtatg tgtgcgtgtc cgcgagtgcc | 540 |
| caccggaggg tctggcaggt atggcgggtg ggcttgggt ctctaacacc tcccttggcc | 600 |
| cgttttccca acccaaagtt aaagcctctg aactggctca agaaatattt gcaatcggga | 660 |
| tggcttctcc tcccaaatct acggtgtttg gtgggttcga acagacctgg cttaagagct | 720 |
| tgtgacctt gagcaagaga ctcaatctct ctgagcttcg gtctcatctg caaagcaggg | 780 |
| taccctaata atggtaaccg gaaacgtccc cgaaactacc ttctcgtacc aggttcttgg | 840 |
| tgaagcactt ggcacgcatc ggagctcatt actcctcatc gtggtcctgt aaggtatgta | 900 |
| gggctgtcac cccattagac agatggggaa accaaggctg aaagaggcca ggtaagctac | 960 |
| ccaaggcaac tggtgtggaa ttgggatgca acccaggtct gtcttcctcc accaatttca | 1020 |
| tgactgtgag aattaagagg gaacttatac gcaaagcgcc tggcacaatc cctaatgttt | 1080 |
| ccttccttct ctcttttccc actccctcct ttccttcctc ccttcaggaa gtttgaggct | 1140 |
| gagacccgaa aagacctggg tgcaagcctc caggcaccct gaagggagtg ggctgagggc | 1200 |
| tggcccaagc tccctcctct ccctctgtag agcctaggat gccctctgc tgcagcggct | 1260 |

| cctgagctc | atg gag ccc tca gcc acc cca ggg gcc cag atg ggg gtc ccc | 1311 |
| | Met Glu Pro Ser Ala Thr Pro Gly Ala Gln Met Gly Val Pro | |
| | 1          5           10 | |
| cct ggc agc aga gag ccg tcc cct gtg cct cca gac tat gaa gat gag | 1359 |
| Pro Gly Ser Arg Glu Pro Ser Pro Val Pro Pro Asp Tyr Glu Asp Glu | |
| 15          20          25          30 | |
| ttt ctc cgc tat ctg tgg cgc gat tat ctg tac cca aaa cag tat gag | 1407 |
| Phe Leu Arg Tyr Leu Trp Arg Asp Tyr Leu Tyr Pro Lys Gln Tyr Glu | |
| 35          40          45 | |
| tgg gtc ctc atc gca gcc tat gtg gct gtg ttc gtc gtg gcc ctg gtg | 1455 |
| Trp Val Leu Ile Ala Ala Tyr Val Ala Val Phe Val Val Ala Leu Val | |
| 50          55          60 | |
| ggc aac acg ctg g gtaggtccag ggcttgcccg gcagtgctgc cggctttccc | 1508 |
| Gly Asn Thr Leu | |
| 65 | |
| tggggattga aggggttgt gtgggaggag ggctcgctga ttaggcagaa ctaggatggg | 1568 |

-continued

```
tgtggctctg ccaccagctt cacctcgctg caccctgcag tc tgc ctg gcc gtg       1622
                                              Val Cys Leu Ala Val
                                                              70 tgg cgg aac cac cac atg agg aca gtc acc aac tac ttc att gtc aac       1670
Trp Arg Asn His His Met Arg Thr Val Thr Asn Tyr Phe Ile Val Asn
                75                      80                  85 ctg tcc ctg gct gac gtt ctg gtg act gct atc tgc ctg ccg gcc agc       1718
Leu Ser Leu Ala Asp Val Leu Val Thr Ala Ile Cys Leu Pro Ala Ser
            90                      95                 100 ctg ctg gtg gac atc act gag tcc tgg ctg ttc ggc cat gcc ctc tgc       1766
Leu Leu Val Asp Ile Thr Glu Ser Trp Leu Phe Gly His Ala Leu Cys
       105                     110                 115 aag gtc atc ccc tat cta cag gtgagctctg cccaggcacc cctcaccact         1817
Lys Val Ile Pro Tyr Leu Gln
120                 125 ccttgtcacg cctgtaaaaa acccacggcc ttgcataggt ctcagtgacc cccagacttg    1877
cctttcagac aggtcagtgg ctcatgaccc ctgaagtgtc atcctctgct gctagcaagg   1937
gcaagccacc agatcagaca ctcgaggaca cagacacaac cccacacact cacagagatc   1997
ccctcctggt cacagccaca gacatataca tagacacgtg tggacatgta tagtcacctc   2057
caggtacaca ggcacacagt caaggagaga ggcaacagcc cacagtgaca catacacgac   2117
accctaggcc tgctccccaa tcccaagggg gcagacgtga ggggcctgat ggaaacagcc   2177
gtctcctctc cctcctgcac tggccaggaa agacccagt ggtggaaacc aggatgtccg    2237
gatggggtta gtggggtgga aggaaggctt ctctcagttt gtatcctgtg atccacttcc   2297
tgcaccccag agggcagggg gcaccccctag aggcaatgcc cacacacctc tgacccagac  2357
tcatctctgc ctcccagaat gagggctttt tcctaacagc ctggggaagg gatggcattc   2417
catggcagag ataaatgcct cttggatttc ccactatttt gaggctcccc actcaactgg   2477
ttaactctgt tgaccctgag cataaagaca gatggatgag ggaattctgt gcctcagttt   2537
cctcatctgt aacagggggg caagagcgct ttgtgggatt gtcatgagga tgatgagaac   2597
agtgcccagc acatagtaag ttacgtaggt gcaagttatt attcaccgga ggggtgcacc   2657
taccatgtgc caggtctaaa gctggacatt gttttgtacat gatttcactt attcgcacaa   2717
gaatcttgcc aggtagatgg tatattccca ttctgtagac gaggctcaga gagggtgagt   2777
gacttgccca catttacaca gccagtaagt ggtggagtca ggatttgcac tgccctgcac   2837
ctgccgtcag cctcctcact cacctactct cacatcgctg ggtggccccc aaaatgaccg   2897
acgttgtgtc cccgtggggc ag gct gtg tcc gtg tca gtg gca gtg cta act    2949
                       Ala Val Ser Val Ser Val Ala Val Leu Thr
                                      130                  135 ctc agc ttc atc gcc ctg gac cgc tgg tat gcc atc tgc cac cca cta     2997
Leu Ser Phe Ile Ala Leu Asp Arg Trp Tyr Ala Ile Cys His Pro Leu
            140                     145                 150 ttg ttc aag agc aca gcc cgg cgg gcc cgt ggc tcc atc ctg ggc atc     3045
Leu Phe Lys Ser Thr Ala Arg Arg Ala Arg Gly Ser Ile Leu Gly Ile
        155                     160                 165 tgg gct gtg tcg ctg gcc atc atg gtg ccc cag gct gca gtc atg gaa     3093
Trp Ala Val Ser Leu Ala Ile Met Val Pro Gln Ala Ala Val Met Glu
    170                     175                 180 tgc agc agt gtg ctg cct gag cta gcc aac cgc aca cgg ctc ttc tca     3141
Cys Ser Ser Val Leu Pro Glu Leu Ala Asn Arg Thr Arg Leu Phe Ser
185                     190                 195                 200 gtc tgt gat gaa cgc tgg gca g gtaatggtgg aagcctcaag caggcatccc      3193
Val Cys Asp Glu Arg Trp Ala
            205
```

```
ctcaggtggg cactttggga gcacgtaccc ctaggacagg catctagcag ggtcccttcc    3253
aaagtgggaa atcccagagc aggtatttcc ctaggggaca ccctagactg gctcctacca    3313
gggatactcc cagggtgggt gcctccctc atgtagacat ctgctctagt gtagatgtcc     3373
ttccaggagg gacaacccaa gttggacaac tccaggtct ctgtctgtca tggtggctgt     3433
atggggtcca gctgctccta ggccttgctt tggccgtagt caggacaggg tggcattgct    3493
aaccagggca gggtggggct cacggattgg gcctgactct gcatctcttg accctgcag    3553
```

| at | gac | ctc | tat | ccc | aag | atc | tac | cac | agt | tgc | ttc | ttt | att | gtc | acc | 3600 |
|---|---|---|---|---|---|---|---|---|---|---|---|---|---|---|---|---|
| Asp | Asp | Leu | Tyr | Pro | Lys | Ile | Tyr | His | Ser | Cys | Phe | Phe | Ile | Val | Thr | |
| | | | 210 | | | | 215 | | | | 220 | | | | | |

| tac | ctg | gcc | cca | ctg | ggc | ctc | atg | gcc | atg | gcc | tat | ttc | cag | ata | ttc | 3648 |
|---|---|---|---|---|---|---|---|---|---|---|---|---|---|---|---|---|
| Tyr | Leu | Ala | Pro | Leu | Gly | Leu | Met | Ala | Met | Ala | Tyr | Phe | Gln | Ile | Phe | |
| | 225 | | | | | 230 | | | | | 235 | | | | | |

| cgc | aag | ctc | tgg | ggc | cgc | cag | gtgaggccca ctctgggcag ggctaggcc | 3699 |
|---|---|---|---|---|---|---|---|---|
| Arg | Lys | Leu | Trp | Gly | Arg | Gln | | |
| 240 | | | | | 245 | | | |

```
agtcactgtg tgggctgggg gtgggagggc tactggtcta actgagtagg cagtcctctg    3759
ccatcagcac atgccatctt ggctgcaacc aaagagaggg gaagcccaga gacacgtcaa    3819
actcaaggcc aaaagcacca gtggctaccc tggaatggaa tagtaacacg tccttctatt    3879
agtggttggc gtttattgaa gtatccactc ccagataatc ttgcatcctc ttagccacca    3939
tatattaccc acattaaata tatgagaaaa ccgagaccca aagatcaac ataacttccc     3999
ccaaaccact cagctagtga gtagatcagg aactaaagcc cagatctgtg agctcccact    4059
gctcagttta gtaccactgc aacaataata atagcaactc cgtggtgctt gccaaattag    4119
gcactttgca tccaatgtct taacaactat ctaacaaaag aagcaacatt acccacgtca    4179
caaatgccaa ataagggcaa ccaacttgcc agattcaaca gcagcagagc cttctggttc    4239
cagggcctgt cttctttcct gcattacaga ctgacccacg gtgggtttct taggtttttg    4299
gggggcaggg gtggtcagag gcccttggcc tagcgagtgg gagtcctgga ttggcgtctg    4359
ggcggtgaga aaaggcaggc cagaacatga ccaggctcag gaagggactc tcacacttgg    4419
ggatgtcacc tacattccac aggaagtact ggcttgcacc caggccatgc cgggcagcgg    4479
atggggacac ggactggctg tgacccaggt cctgccttgg aggagcaccc agtccagtag    4539
gacccttcct gactgccag ccctgtagtc caccaacact catcatctgc tcccacaga     4599
ccccccagcc aagcaggaca caggcacgat cctcctcatt tgacagatat gaaagcaagg    4659
cttagaaagg aaaatgaggt ggctaaggtc acatagctca cgaatggctg agctggctct    4719
agacccgcgt ttccagaact ccagccccat gcccctctgt ggtgggtgat ttgagtgtcc    4779
ggtggcagga gaggcttctc caggagccca gaaccacccc aggcttatgg gcactggccc    4839
aggccattcg atgctgccca cctgctcacc ccttgcccag gcctcctcat agtctggtat    4899
gatccagggg aggcacaact cacccccacc cctaccctca agatagtgt tggagattta     4959
gggaggatgt atgggcagtt gacaggatgt ggcctgggt cttgtcaagg ttccccacct     5019
ctttgagtct tagttgcctc atctatacct aaggaccaat aatatctttc cacaaggcgt    5079
gttgtagagg gtttcacaaa gagctaatgg aaaatgaaag tctaggctgg gcgcagtggc    5139
tcacacctgt attcccagca ctttgggagg ctgaggcagg cggatcacct aaggtcagga    5199
gttcaagacc agcctggcca acgtggtgaa accccatctc tactaaaaat acaaaactta    5259
gcccggtgtg gtggcgcaca cctgtaatcc cagctactcg ggaggcgaga ttgaagagag    5319
```

```
                                      -continued ccaagattgc accattgcac tccagcttag gtgacaagag tgaaatgcca tctcaaaaaa      5379
aaaaaaaaag aaagaaaag aaaatgaaag tctatcgttc actctcaagt ccagagtgtt      5439
agtctatcat aaacattaga ttccttcctc ttgcaagggt tttatccttt tgcccatctc      5499
caccctgccc ggggtccagc ctggagtagg ccccacaaaa ggcaaccacc ctcccaaggt      5559
gctgtaccca ccactgctgt ctctatgtgt gctggacag atc ccc ggc acc acc        5613
                                          Ile Pro Gly Thr Thr
                                                          250 tca gca ctg gtg cgg aac tgg aag cgc ccc tca gac cag ctg ggg gac       5661
Ser Ala Leu Val Arg Asn Trp Lys Arg Pro Ser Asp Gln Leu Gly Asp
        255                 260                 265 ctg gag cag ggc ctg agt gga gag ccc cag ccc cgg gcc cgc gcc ttc       5709
Leu Glu Gln Gly Leu Ser Gly Glu Pro Gln Pro Arg Ala Arg Ala Phe
    270                 275                 280 ctg gct gaa gtg aag cag atg cgt gca cgg agg aag aca gcc aag atg       5757
Leu Ala Glu Val Lys Gln Met Arg Ala Arg Arg Lys Thr Ala Lys Met
285                 290                 295 ctg atg gtg gtg ctg ctg gtc ttc gcc ctc tgc tac ctg ccc atc agc       5805
Leu Met Val Val Leu Leu Val Phe Ala Leu Cys Tyr Leu Pro Ile Ser
300                 305                 310                 315 gtc ctc aat gtc ctt aag ag gtgagagcac ggggtatggt tggggtgggg          5855
Val Leu Asn Val Leu Lys Arg
                320 agaagtttga ggttggggaa ggagctctcc ttgcttggga gaaagacctg gctccacccc      5915 ttctccacta tgtgatcttg gcaggccat ttctcttctc tgagcctcca tctcctaggg      5975 ctatcgtgaa aattcacgca ttcattcact taatcatcac attttagggg gctggaaata      6035 caatgaacaa gtgcataaga cagacaaagt ccctgccttc atggaggctg cattctagca      6095 ggagagaagg gaagtaaata gaagaatcaa tgtatattat aatgtcaggc agtgataact      6155 gctgggaaga aaaataaaat aggacagaga gtgacaatga taagggttgg tgggttttg      6215 cttttgcttt agatacaatg gtttaaaaaa agcaggggc cgggtgcagt ggctcacatc      6275 tgtaatccca acacgttggg aggccaagga gggaggatcg cttgaggcca ggagttcaag      6335 atcagcccgg gcaacataat gagacttcgt ctctactaaa attcaaaaaa ttagccagcc      6395 atggtggcat gtgcctgtag ttctagctac acagactgag gtggaagaat agcttgagcc      6455 caggaggttg aggctgcagc gaaccatgat tgcaccactg cactccagcc tgggtgacac      6515 agctgtctca aaaaaaaaaa aaaaaaaaaa aaagcctttc caaggaaatg acatttgagc      6575 agagacttga aggaagtgag agagctaacc atgcacgtgt ctgtagggac agccaaagag      6635 ggtcgcaggg cgctggggag agaatgcagg ctattggaca gaagacagtt tcactttgag      6695 attgtgcttg gccacttcct ggttgtgtga tcttcggcat gtcactttac ttctctgagc      6755 ctcagtttcc ttaatggaaa aatggatgat gtctatgatt catcatgttg ctgtgaggat      6815 ggatgagaaa gtggatggga agccccaggg gatccgatgg ccaggaggct agagatgccc      6875 atcacggtgc ttgataccct ccatgcttga gaaccccaaa ccctggccaa gacctcaggt      6935 acagaaggcc aggaaacgtg gacagaagtg ggcagtagga actcttgcac tttacagctc      6995 aggttctgtg agcagcactc ccccagtaca tgcatacgca gctacccat ttctgacgct       7055 cctccaccct gggcctag g gtg ttc ggg atg ttc cgc caa gcc agt gac cgc     7107
                   Val Phe Gly Met Phe Arg Gln Ala Ser Asp Arg
                                   325                 330 gaa gct gtc tac gcc tgc ttc acc ttc tcc cac tgg ctg gtg tac gcc       7155
Glu Ala Val Tyr Ala Cys Phe Thr Phe Ser His Trp Leu Val Tyr Ala
    335                 340                 345
```

-continued

```
aac agc gct gcc aac ccc atc atc tac aac ttc ctc agt g gtgagcaggc        7205
Asn Ser Ala Ala Asn Pro Ile Ile Tyr Asn Phe Leu Ser
350                 355                 360 tggggatgca aaatgactga gggtggccaa cagtccacat gacaagtctc ccatcccca         7265 agccagggcc caaataaagg atggtgggtg aggatgtacc tgctgtgggc acagtgatcc        7325
tgctctggga ggacccaccc caagcggccc tggcctgagt gggagacggg ccacactccc       7385
tacagtggct ggcacccagg atccagtttt gcagattctg cagaccagtg agtgagtgga       7445
agggcagggg ctaggccagc tcaccccaa ctcccaccct gggtgcaggc acagcaagac        7505
ctccaatcag ctcaggcaga ggagtccatc ctccccggag ggagtcagac ctgtgggagg       7565
agggccctgg agccctgcc cgaggaagga ttgcacagtc caggtgtcag ggctaaagta        7625
gggtcactct gagagacaag ccaggcccag ggaagggctt cgccggctca gctagacaca       7685
ctggcagagt gaccggaatc tcaggggttg tcccctctgg aagtcttcct ccctgccac        7745 ccccactccc actccaggcc tctcctctct gctgtcccac agtgcccacc ccctccctct       7805
acctcccagt ctcagggtgg taatggctct gaggctgagc tcagcagaag tctgactcac      7865
cagccctctg actttgggaa tagacttcta aagaacaggt ccagatgact gttgaagcct       7925
ggacagaaat aatctttgag gaactattaa aaggttaaag aaaggatcag gagtcaatag       7985
tataaccctc attgagactc aagaattact caacaaggct ggctgcgggt ttccaggtca      8045
gaaaagagaa tagatgatga gctgtgtggg gaggggaggg cagacagact tactgacaca      8105
tatgcctttg tttggcctat gtttactgag cacctactat gtgcttgacc ctgtgctggg       8165
caccagagag gctggcagcc taatgacaca tgatcaaagg ggcttcagcc tgacaaaatc      8225
tgtttccctg gtatacttgg gctgaataat gtggtgtggt ggtccctcct tccctcctcc      8285
cccttgagaa gggctttgga attagaattg ggttcagctt ctggctgggt ggacttgggc      8345
aagccactgt acctctgtgc atctcatctg tgaagtgagg ataaaggact ccagcctttc      8405
agggtgctgg gatgctctgg cggacagagg ctgaggcgcc cagcacagcg tgactgccaa      8465
atgcaaaagg gctgctgctg ccgtcatttt catcatcaaa gggcagagag gacacaagcc      8525
tcgcaacaga tagtgacccc cacgtacaca ccaaggagag cagaggtgac ctgaggcccc      8585
cgagccagac accacgtttt gagtcagcct ccgagccaga gcacagtcaa ggaatcagat      8645
ggcaattgcg tctctccttg gaacccgct ccagggcttc tgtcctctct ctctggcggt       8705
gccgaggttg cctcagggct ctccctccca gctctatccc tccctccctc ccgcccct       8765 cataggcagc ttggctggag ctgcgtgggt gtccctgggc tcaaggcccc ttcctgctgc      8825
atctgtctcc ttatggctgt gtcttttgtc tcccaaccaa g gc aaa ttc cgg gag        8880
                                             Gly Lys Phe Arg Glu
                                                         365 cag ttt aag gct gcc ttc tcc tgc tgc ctg cct ggc ctg ggt ccc tgc        8928
Gln Phe Lys Ala Ala Phe Ser Cys Cys Leu Pro Gly Leu Gly Pro Cys
        370                 375                 380 ggc tct ctg aag gcc cct agt ccc cgc tcc tct gcc agc cac aag tcc        8976
Gly Ser Leu Lys Ala Pro Ser Pro Arg Ser Ser Ala Ser His Lys Ser
    385                 390                 395 ttg tcc ttg cag agc cga tgc tcc atc tcc aaa atc tct gag cat gtg        9024
Leu Ser Leu Gln Ser Arg Cys Ser Ile Ser Lys Ile Ser Glu His Val
400                 405                 410                 415 gtg ctc acc agc gtc acc aca gtg ctg ccc tga gcgagggctg ccctggaggc      9077
Val Leu Thr Ser Val Thr Thr Val Leu Pro  *
                420                 425
```

-continued

```
tccggctcgg gggatctgcc cctacccctc atggaaagac agctggatgt ggtgaaaggc    9137
tgtggcttca gtcctgggtt tctgcctgtg tgactctgga taagtcactt cctctgtctg    9197
agcttgtgtc ccctaagcag ggttgatgtg aggattaagc atgctgaagc aagtggaaag    9257
ctccttgtaa actgtgaagt gttgtggaca tgattattgt tgtacttctc tcatttggcc    9317 atacccaca gtataatctg tccccatcct ccttccagag cttggtcatc ctcctaaaga    9377
cccctttcct acccaattac aggccttccc tggagtctgc tctaaaggtc ccaacaggca    9437
tttccatctt gttccatggc tccctgaagc ccagggctgc acttggccag ctgttctgat    9497
gcctgtgtga actaatctgg gcccagcctt tctccagcgg gccacgagca cagccccacc    9557
ctaaccaggt gccaagggca cacaccacag acccgacctt gttggctttg tggtgtgata    9617
aaacactctc catggccact tggcagagag gccagcagcc cgaagcaact gtaattaaaa    9677
gcctggcact gaatgttccc tttccttgtc attgcacaaa atctgtgctg cttaggttag    9737
gagcagaaga aggtggggaa gctgggggga gggaagacaa gaaggcac                 9785
```

<210> SEQ ID NO 2
<211> LENGTH: 425
<212> TYPE: PRT
<213> ORGANISM: Homo Sapiens

<400> SEQUENCE: 2

```
Met Glu Pro Ser Ala Thr Pro Gly Ala Gln Met Gly Val Pro Pro Gly
 1               5                  10                  15

Ser Arg Glu Pro Ser Pro Val Pro Pro Asp Tyr Glu Asp Glu Phe Leu
            20                  25                  30

Arg Tyr Leu Trp Arg Asp Tyr Leu Tyr Pro Lys Gln Tyr Glu Trp Val
        35                  40                  45

Leu Ile Ala Ala Tyr Val Ala Val Phe Val Val Ala Leu Val Gly Asn
    50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
                85                  90                  95

Ala Ile Cys Leu Pro Ala Ser Leu Leu Val Asp Ile Thr Glu Ser Trp
            100                 105                 110

Leu Phe Gly His Ala Leu Cys Lys Val Ile Pro Tyr Leu Gln Ala Val
        115                 120                 125

Ser Val Ser Val Ala Val Leu Thr Leu Ser Phe Ile Ala Leu Asp Arg
    130                 135                 140

Trp Tyr Ala Ile Cys His Pro Leu Leu Phe Lys Ser Thr Ala Arg Arg
145                 150                 155                 160

Ala Arg Gly Ser Ile Leu Gly Ile Trp Ala Val Ser Leu Ala Ile Met
                165                 170                 175

Val Pro Gln Ala Ala Val Met Glu Cys Ser Ser Val Leu Pro Glu Leu
            180                 185                 190

Ala Asn Arg Thr Arg Leu Phe Ser Val Cys Asp Glu Arg Trp Ala Asp
        195                 200                 205

Asp Leu Tyr Pro Lys Ile Tyr His Ser Cys Phe Phe Ile Val Thr Tyr
    210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
                245                 250                 255
```

```
Asn Trp Lys Arg Pro Ser Asp Gln Leu Gly Asp Leu Glu Gln Gly Leu
            260                 265                 270
Ser Gly Glu Pro Gln Pro Arg Ala Arg Ala Phe Leu Ala Glu Val Lys
            275                 280                 285
Gln Met Arg Ala Arg Arg Lys Thr Ala Lys Met Leu Met Val Val Leu
            290                 295                 300
Leu Val Phe Ala Leu Cys Tyr Leu Pro Ile Ser Val Leu Asn Val Leu
305                 310                 315                 320
Lys Arg Val Phe Gly Met Phe Arg Gln Ala Ser Asp Arg Glu Ala Val
                325                 330                 335
Tyr Ala Cys Phe Thr Phe Ser His Trp Leu Val Tyr Ala Asn Ser Ala
            340                 345                 350
Ala Asn Pro Ile Ile Tyr Asn Phe Leu Ser Gly Lys Phe Arg Glu Gln
            355                 360                 365
Phe Lys Ala Ala Phe Ser Cys Cys Leu Pro Gly Leu Gly Pro Cys Gly
            370                 375                 380
Ser Leu Lys Ala Pro Ser Pro Arg Ser Ser Ala Ser His Lys Ser Leu
385                 390                 395                 400
Ser Leu Gln Ser Arg Cys Ser Ile Ser Lys Ile Ser Glu His Val Val
                405                 410                 415
Leu Thr Ser Val Thr Thr Val Leu Pro
            420                 425

<210> SEQ ID NO 3
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 3
tcaggaagtt tgaggctgag a                                         21

<210> SEQ ID NO 4
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 4
atcctaggct ctacagaggg a                                         21

<210> SEQ ID NO 5
<211> LENGTH: 22
<212> TYPE: DNA
<213> ORGANISM: Artificial Sequence
<220> FEATURE:
<223> OTHER INFORMATION: nucleic acid primers based on human mRNA
      sequence

<400> SEQUENCE: 5
gaagatgagt ttctccgcta tc                                        22

<210> SEQ ID NO 6
<211> LENGTH: 21
<212> TYPE: DNA
<213> ORGANISM: Artificial Sequence
<220> FEATURE:
```

-continued

```
<223> OTHER INFORMATION: nucleic acid primers based on human mRNA
      sequence

<400> SEQUENCE: 6
gatgaggacc cactcatact g                                                    21

<210> SEQ ID NO 7
<211> LENGTH: 22
<212> TYPE: DNA
<213> ORGANISM: Artificial Sequence
<220> FEATURE:
<223> OTHER INFORMATION: nucleic acid primers based on human mRNA
      sequence

<400> SEQUENCE: 7
acatgaggac agtcaccaac ta                                                   22

<210> SEQ ID NO 8
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 8
cagatagcag tcaccagaac g                                                    21

<210> SEQ ID NO 9
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 9
acatcactga gtcctggctg t                                                    21

<210> SEQ ID NO 10
<211> LENGTH: 22
<212> TYPE: DNA
<213> ORGANISM: Artificial Sequence
<220> FEATURE:
<223> OTHER INFORMATION: nucleic acid primers based on human mRNA
      sequence

<400> SEQUENCE: 10
atgaagctga gagttagcac tg                                                   22

<210> SEQ ID NO 11
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 11
ctattgttca agagcacagc c                                                    21

<210> SEQ ID NO 12
<211> LENGTH: 21
<212> TYPE: DNA
<213> ORGANISM: Artificial Sequence
<220> FEATURE:
<223> OTHER INFORMATION: nucleic acid primers based on human mRNA
```

-continued sequence

<400> SEQUENCE: 12
catcacagac tgagaagagc c                                              21

<210> SEQ ID NO 13
<211> LENGTH: 20
<212> TYPE: DNA
<213> ORGANISM: Artificial Sequence
<220> FEATURE:
<223> OTHER INFORMATION: nucleic acid primers based on human mRNA
      sequence

<400> SEQUENCE: 13
cttcacttca gccaggaagg                                                20

<210> SEQ ID NO 14
<211> LENGTH: 22
<212> TYPE: DNA
<213> ORGANISM: Artificial Sequence
<220> FEATURE:
<223> OTHER INFORMATION: nucleic acid primers based on human mRNA
      sequence

<400> SEQUENCE: 14
aatgtcctta agagggtgtt cg                                             22

<210> SEQ ID NO 15
<211> LENGTH: 22
<212> TYPE: DNA
<213> ORGANISM: Artificial Sequence
<220> FEATURE:
<223> OTHER INFORMATION: nucleic acid primers based on human mRNA
      sequence

<400> SEQUENCE: 15
gaagttgtag atgatggggt tg                                             22

<210> SEQ ID NO 16
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 16
cacaagtcct tgtccttgca g                                              21

<210> SEQ ID NO 17
<211> LENGTH: 22
<212> TYPE: DNA
<213> ORGANISM: Artificial Sequence
<220> FEATURE:
<223> OTHER INFORMATION: nucleic acid primers based on human mRNA
      sequence

<400> SEQUENCE: 17
caccacatgc tcagagattt tg                                             22

<210> SEQ ID NO 18
<211> LENGTH: 20
<212> TYPE: DNA
<213> ORGANISM: Artificial Sequence
<220> FEATURE:
<223> OTHER INFORMATION: nucleic acid primers based on human mRNA
      sequence

```
<400> SEQUENCE: 18 cctaccctc atggaaagac                                                  20

<210> SEQ ID NO 19
<211> LENGTH: 21
<212> TYPE: DNA
<213> ORGANISM: Artificial Sequence
<220> FEATURE:
<223> OTHER INFORMATION: nucleic acid primers based on human mRNA
      sequence

<400> SEQUENCE: 19
atccagagtc acacaggcag a                                               21

<210> SEQ ID NO 20
<211> LENGTH: 17
<212> TYPE: DNA
<213> ORGANISM: Artificial Sequence
<220> FEATURE:
<223> OTHER INFORMATION: nucleic acid primers

<400> SEQUENCE: 20
tgtaaaacga cggccag                                                    17

<210> SEQ ID NO 21
<211> LENGTH: 17
<212> TYPE: DNA
<213> ORGANISM: Artificial Sequence
<220> FEATURE:
<223> OTHER INFORMATION: nucleic acid primers

<400> SEQUENCE: 21
caggaaacag ctatgac                                                    17

<210> SEQ ID NO 22
<211> LENGTH: 22
<212> TYPE: DNA
<213> ORGANISM: Artificial Sequence
<220> FEATURE:
<223> OTHER INFORMATION: nucleic acid primers

<400> SEQUENCE: 22
tctttattgt cacctacctg gc                                              22
```

HUMAN NARCOLEPSY GENE

RELATED APPLICATION(S)

This application is a Continuation-in-Part of U.S. Ser. No. 09/379,083, filed Aug. 23, 1999 now abandoned, the entire teachings of which are incorporated herein by reference.

BACKGROUND OF THE INVENTION

Narcolepsy, a disorder which affects approximately 1 in 2,000 individuals, is characterized by daytime sleepiness, sleep fragmentation, and symptoms of abnormal rapid eye movement (REM) sleep that include cataplexy (loss of muscle tone), sleep paralysis, and hypnagogic hallucinations (Aldrich, M. S., Neurology 42:34–43 (1992); Siegel, J. M., Cell 98:409–412 (1999)). In humans, susceptibility to narcolepsy has been associated with a specific human leukocyte antigen (BLA) alleles, including DQB1*0602 (Mignot, E., Neurology 50:S16–22 (1998); Kadotani, H. et al., Genome Res. 8:427–434 (1998); Faraco, J. et al., J. Hered. 90:129–132 (1999)); however, attempts to verify narcolepsy as an autoimmune disorder have failed (Mignot, E. et al., Adv. Neuroimmunol. 5:23–37 (1995); Mignot, E., Curr. Opin. Pulm. Med. 2:482–487 (1996)). In a canine model of narcolepsy, the disorder is transmitted as an autosomal recessive trait, canarc-1 (Foutz, A. S. et al., Sleep 1:413–421 91979); Baker, T. L. and Dement, W. C., Brain Mechanisms of Sleep (D. J. McGinty et al., eds.s, New York: Raven Press, pp. 199–233 (1985)). The possibility of linkage between canarc-1 and the canine major histocompatibility complex has been excluded (Mignot, E. et al., Proc. Natl. Acad. Sci. USA 88:3475–3478 (1991)).

A mutation in the hypocretin (orexin) receptor 2 gene in canines has been identified in narcolepsy (Lin, L. et al., Cell 98:365–376 (1999)); Hypocrexins/orexins (orexin-A and -B) are neuropeptides associated with regulation of food consumption (de Lecea, L., et al., Proc. Natl. Acad. Sci. USA 95:322–327 (1998); Sakurai, T. et al, Cell 92:573–585 (1998)) as well as other possible functions (Peyron, C. et al., J. Neurosci. 18:9996–10015 (1998)). Human cDNA of receptors for orexins have been cloned (Sakurai, T. et al., Cell 92:573–585 (1998)), however, full human genes for the orexin receptors have not yet been identified.

Diagnosis of narcolepsy is difficult, as it is necessary to distinguish narcolepsy from other conditions such as chronic fatigue syndrome or other sleep disorders (Ambrogetti, A. and Olson, L. C., Med. J. Aust. 160:426–429 (1994); Aldrich, M. S., Neurology 50:S2–7 (1998)). Methods of diagnosing narcolepsy based on specific criteria would facilitate identification of the disease, reduce the time and expense associated with diagnosis, and expedite commencement of treatment.

SUMMARY OF THE INVENTION

As described herein, a full gene for the human hypocretin (orexin) receptor 1 (HCRTR1) has been identified. The sequence of the HCRTR1 gene as described herein is shown in FIG. 1 (SEQ ID NO: 1). Accordingly, this invention pertains to an isolated nucleic acid molecule containing the HCRTR1 gene. The invention also relates to DNA constructs comprising the nucleic acid molecules described herein operatively linked to a regulatory sequence, and to recombinant host cells, such as bacterial cells, fungal cells, plant cells, insect cells and mammalian cells, comprising the nucleic acid molecules described herein operatively linked to a regulatory sequence. The invention also pertains to methods of diagnosing narcolepsy in an individual. The methods include detecting the presence of a mutation in the HCRTR1 gene. The invention additionally pertains to pharmaceutical compositions comprising the HCRTR1 nucleic acids of the invention. The invention further pertains to methods of treating narcolepsy, by administering HCRTR1 nucleic acids of the invention or compositions comprising the HCRTR1 nucleic acids. The methods of the invention allow the accurate diagnosis of narcolepsy and reduce the need for time-consuming and expensive sleep laboratory assessments.

BRIEF DESCRIPTION OF THE DRAWINGS

FIGS. 1A–1E depict the sequence of the human orexin receptor 1 gene (SEQ ID NO:1) and the encoded receptor (SEQ ID NO:2).

The foregoing and other objects, features and advantages of the invention will be apparent from the following more particular description of preferred embodiments of the invention, as illustrated in the accompanying drawings.

DETAILED DESCRIPTION OF THE INVENTION

The present invention relates to a human hypocretin (orexin) receptor 1 (HCRTR1) gene, and the relationship of the gene to narcolepsy. As described herein, Applicants have isolated the HCRTR1 gene. The gene and its products are implicated in the pathogenesis of narcolepsy, as mutations in a closely related receptor, hypocretin (orexin) receptor 2, have been associated with the presence of narcolepsy in a well-established canine model of narcolepsy (Lin, L. et al., Cell 98:365–376 (1999)).

NUCLEIC ACIDS OF THE INVENTION

Accordingly, the invention pertains to an isolated nucleic acid molecule containing the human HCRTR1 gene. The term, "HCRTR1 gene," refers to an isolated genomic nucleic acid molecule that encodes the human hypocretin (orexin) receptor 1. As used herein, the term, "genomic nucleic acid molecule" indicates that the nucleic acid molecule contains introns and exons as are found in genomic DNA (i.e., not cDNA). The nucleic acid molecules can be double-stranded or single-stranded; single stranded nucleic acid molecules can be either the coding (sense) strand or the non-coding (antisense) strand. The nucleic acid molecule can additionally contain a marker sequence, for example, a nucleotide sequence which encodes a polypeptide, to assist in isolation or purification of the polypeptide. Such sequences include, but are not limited to, those which encode a glutathione-S-transferase (GST) fusion protein and those which encode a hemaglutinin A (HA) peptide marker from influenza. In a preferred embodiment, the nucleic acid molecule has the sequence shown in FIGS. 1A–1E (SEQ ID NO:1).

As used herein, an "isolated" or "substantially pure" gene or nucleic acid molecule is intended to mean a gene which is not flanked by nucleotide sequences which normally (in nature) flank the gene (as in other genomic sequences). Thus, an isolated gene can include a gene which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the HCRTR1 gene in tissue (e.g., human tissue), such as by Northern blot analysis.

The present invention also encompasses variations of the nucleic acid sequences of the invention. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the hypocretin (orexin) receptor 1.

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequences via hydrogen bonding and other chemical interactions. Such molecules include, for example, those in which peptide linkages substitute for phosphate linkages in the backbone of the molecule.

The invention also relates to fragments of the isolated nucleic acid molecules described herein. The term "fragment" is intended to encompass a portion of a nucleic acid sequence described herein which is from at least about 25 contiguous nucleotides to at least about 50 contiguous nucleotides or longer in length. One or more introns can also be present. Such fragments are useful as probes, e.g., for diagnostic methods, as described below and also as primers or probes. Particularly preferred primers and probes selectively hybridize to a nucleic acid molecule containing the HCRTR1 gene described herein.

The invention also pertains to nucleic acid molecules which hybridize under high stringency hybridization conditions, such as for selective hybridization, to a nucleotide sequence described herein (e.g., nucleic acid molecules which specifically hybridize to a nucleic acid containing the HCRTR1 gene described herein). Hybridization probes are oligonucleotides which bind in a base-specific manner to a complementary strand of nucleic acid. Suitable probes include polypeptide nucleic acids, as described in (Nielsen el al., *Science* 254, 1497–1500 (1991)).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1–2.10.16 and pages 6.3.1–6 in *Current Protocols in Molecular Biology* (Ausubel, F. M. et al., "*Current Protocols in Molecular Biology*", John Wiley & Sons, (1998)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

Hybridizable nucleic acid molecules are useful as probes and primers, e.g., for diagnostic applications, as described below. As used herein, the term "primer" refers to a single-stranded oligonucleotide which acts as a point of initiation of template-directed DNA synthesis under appropriate conditions (e.g., in the presence of four different nucleoside triphosphates and an agent for polymeriatizon, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleotide sequences which have a substantial identity with the nucleotide sequences described herein; particularly preferred are nucleotide sequences which have at least about 70%, and more preferably at least about 80% identity, and even more preferably at least about 90% identity, with nucleotide sequences described herein. Particularly preferred in this instance are nucleotide sequences encoding hypocretin (orexin) receptor 1.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin et al. (*Proc. Natl. Acad. Sci. USA,* 90:5873–5877 (1993)). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al. (*Nucleic Acids Res,* 25:3389–3402 (1997)). When utilizing BLAST and Gapped BLAST programs, the default parameters of the respective programs (e.g., NBLAST) can be used. See http://www.ncbi.nlm.nih.gov. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

The invention also provides expression vectors containing a nucleic acid comprising the HCRTR1 gene, operatively linked to at least one regulatory sequence. Many such vectors are commercially available, and other suitable vectors can be readily prepared by the skilled artisan. "Operatively linked" is intended to mean that the nucleic acid sequence is linked to a regulatory sequence in a manner which allows expression of the nucleic acid sequence. Regulatory sequences are art-recognized and are selected to produce a hypocretin (orexin) receptor 1. Accordingly, the term "regulatory sequence" includes promoters, enhancers, and other expression control elements such as those described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the receptor desired to be expressed. For instance, the gene of the present invention can be expressed by ligating the gene into a vector suitable for expression in either prokaryotic cells, eukaryotic cells or both (see, for example, Broach, et al., *Experimental Manipulation of Gene Expression,* ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Vectors can also include, for example, an autonomously replicating sequence (ARS), expression control sequences, ribosome-binding sites, RNA splice sites, polyadenylation sites, transcriptional terminator sequences, secretion signals and mRNA stabilizing sequences.

Prokaryotic and eukaryotic host cells transformed by the described vectors are also provided by this invention. For instance, cells which can be transformed with the vectors of the present invention include, but are not limited to, bacterial cells such as *E. coli* (e.g., *E. coli* K12 strains), Streptomyces, Pseudomonas, *Serratia marcescens* and *Salmonella typhimurium,* insect cells (baculovirus), including Drosophila, fungal cells, such as yeast cells, plant cells and mammalian cells, such as thymocytes, Chinese hamster ovary cells (CHO), and COS cells. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host.

The nucleic acid molecules of the present invention can be produced, for example, by replication in a suitable host cell, as described above. Alternatively, the nucleic acid molecules can also be produced by chemical synthesis.

The nucleotide sequences of the nucleic acid molecules described herein (e.g., a nucleic acid molecule comprising SEQ ID NO:1) can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA,* 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabeled and used as a probe for screening a library or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual,* (Acad. Press, 1988)). Using these or similar methods, the protein(s) and the DNA encoding the protein can be isolated, sequenced and further characterized.

METHODS OF DIAGNOSIS

The nucleic acids and the proteins described above can be used to detect, in an individual, a mutation in the HCRTR1 gene that is associated with narcolepsy. In one embodiment of the invention, diagnosis of narcolepsy is made by detecting a mutation in the HCRTR1 gene. The mutation can be the insertion or deletion of a single nucleotide, or of more than one nucleotide, resulting in a frame shift mutation; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene. More than one such mutation may be present in a single gene. Such sequence changes cause a mutation in the receptor encoded by the HCRTR1 gene. For example, if the mutation is a frame shift mutation, the frame shift can result in a change in the encoded amino acids, and/or can result in the generation of a premature stop codon, causing generation of a truncated receptor. Alternatively, a mutation associated with narcolepsy can be a synonymous mutation in one or more nucleotides (i.e., a mutation that does not result in a change in the receptor encoded by the HCRTR1 gene). Such a polymorphism may alter splicing sites, affect the stability or transport of mRNA, or otherwise affect the transcription or translation of the gene. A HCRTR1 gene that has any of the mutations described above is referred to herein as a "mutant gene." It is likely that a mutation in the HCRTR1 gene is associated with narcolepsy in humans because of the association between a mutation in the HCRTR1 gene and narcolepsy in dogs (Lin, L. et al., *Cell* 98:365–376 (1999), the entire teachings of which are incorporated herein by reference). In a preferred embodiment, the mutation in the HCRTR1 gene is to a deletion mutation, for example, a deletion that corresponds to the deletions found in the hypocretin (orexin) receptor 2 in narcoleptic dogs as described by Lin et al., supra (e.g., a deletion of one or more exons, such as a deletion of the fourth exon, that can be caused by insertion of one or more nucleotides upstream of the splice site of the exon, or a deletion of exon 6, that can be caused by a G to A transition in the splice junction consensus sequence). In another preferred embodiment, the mutation in the HCRTR1 gene is mutation that effects a "knockout" of the entire gene, such as deletion of the first exon as described by Chemelli, R. M. et al, (*Cell* 98:437–451 (1999), the entire teachings of which are incorporated herein).

In a first method of diagnosing narcolepsy, hybridization methods, such as Southern analysis, are used (see Current Protocols in Molecular Biology, Ausubel, F. et al., eds., John Wiley & Sons, including all supplements through 1999). For example, a test sample of genomic DNA, RNA, or cDNA, is obtained from an individual suspected of having (or carrying a defect for) narcolepsy (the "test individual"). The individual can be an adult, child, or fetus. The test sample can be from any source which contains genomic DNA, such as a blood sample, sample of amniotic fluid, sample of cerebrospinal fluid, or tissue sample from skin, muscle, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined to determine whether a mutation in the HCRTR1 gene is present. The presence of the mutation can be indicated by hybridization of the gene in the test sample to a nucleic acid probe. A "nucleic acid probe", as used herein, can be a DNA probe or an RNA probe; the nucleic acid probe contains at least one mutation in the HCRTR1 gene. The probe can be one of the nucleic acid molecules described above (e.g., the gene, a vector comprising the gene, etc.)

To diagnose narcolepsy by hybridization, a hybridization sample is formed by contacting the test sample containing a HCRTR1 gene, with at least one nucleic acid probe. The hybridization sample is maintained under conditions which are sufficient to allow specific hybridization of the nucleic acid probe to the HCRTR1 gene. "Specific hybridization", as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and the HCRTR1 gene in the test sample, then the HCRTR1 gene has the mutation that is present in the nucleic acid probe. More than one nucleic acid probe can also be used concurrently in this method. Specific hybridization of any one of the nucleic acid probes is indicative of a mutation in the HCRTR1 gene, and is therefore diagnostic for narcolepsy.

In another hybridization method, Northern analysis (see Current Protocols in Molecular Biology, Ausubel, F. et al., eds., John Wiley & Sons, supra) is used to identify the presence of a mutation associated with narcolepsy. For Northern analysis, a test sample of RNA is obtained from the individual by appropriate means. Specific hybridization of a nucleic acid probe, as described above, to RNA from the individual is indicative of a mutation in the HCRTR1 gene, and is therefore diagnostic for narcolepsy For representative examples of use of nucleic acid probes, see, for example, U.S. Pat. Nos. 5,288,611 and 4,851,330. Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry,* 1994, 5, American Chemical Society, p.1(1994). The PNA probe can be designed to specifically hybridize to a gene having a polymorphism associated with autoimmune disease. Hybridization of the PNA probe to the HCRTR1 gene is diagnostic for narcolepsy.

In another method of the invention, mutation analysis by restriction digestion can be used to detect mutant genes, or genes containing polymorphisms, if the mutation or polymorphism in the gene results in the creation or elimination of a restriction site. A test sample containing genomic DNA is obtained from the individual. Polymerase chain reaction (PCR) can be used to amplify the HCRTR1 gene (and, if necessary, the flanking sequences) in the test sample of genomic DNA from the test individual. RFLP analysis is conducted as described (see Current Protocols in Molecular Biology, supra). The digestion pattern of the relevant DNA fragment indicates the presence or absence of the mutation in the HCRTR1 gene, and therefore indicates the presence or absence of narcolepsy.

Sequence analysis can also be used to detect specific mutations in the HCRTR1 gene. A test sample of DNA is obtained from the test individual. PCR can be used to amplify the gene, and/or its flanking sequences. The sequence of the HCRTR1 gene, or a fragment of the gene is determined, using standard methods. The sequence of the gene (or gene fragment) is compared with the nucleic acid sequence of the gene, as described above. The presence of a mutation in the HCRTR1 gene indicates that the individual has narcolepsy.

Allele-specific oligonucleotides can also be used to detect the presence of a mutation in the HCRTR1 gene, through the use of dot-blot hybridization of amplified proteins with allele-specific oligonucleotide (ASO) probes (see, for example, Saiki, R. et al., (1986), Nature (London) 324:163–166). An "allele-specific oligonucleotide" (also referred to herein as an "allele-specific oligonucleotide probe") is an oligonucleotide of approximately 10–50 base pairs, preferably approximately 15–30 base pairs, that specifically hybridizes to the HCRTR1 gene, and that contains a mutation associated with narcolepsy. An allele-specific oligonucleotide probe that is specific for particular mutation in the HCRTR1 gene can be prepared, using standard methods (see Current Protocols in Molecular Biology, supra). To identify mutations in the gene that are associated with narcolepsy, a test sample of DNA is obtained from the individual. PCR can be used to amplify all or a fragment of the HCRTR1 gene, and its flanking sequences. The DNA containing the amplified HCRTR1 gene (or fragment of the gene) is dot-blotted, using standard methods (see Current Protocols in Molecular Biology, supra), and the blot is contacted with the oligonucleotide probe. The presence of specific hybridization of the probe to the amplified HCRTR1 gene is then detected. Specific hybridization of an allele-specific oligonucleotide probe to DNA from the individual is indicative of a mutation in the HCRTR1 gene, and is therefore indicative of narcolepsy.

Other methods of nucleic acid analysis can be used to detect mutations in the HCRTR1 gene, for the diagnosis of narcolepsy. Representative methods include direct manual sequencing; automated fluorescent sequencing; single-stranded conformation polymorphism assays (SSCA); clamped denaturing gel electrophoresis (CDGE) heteroduplex analysis; chemical mismatch cleavage (CMC); RNase protection assays; use of proteins which recognize nucleotide mismatches, such as E. coli mutS protein; allele-specific PCR, and other methods.

PHARMACEUTICAL COMPOSITIONS

The present invention also pertains to pharmaceutical compositions comprising nucleic acids described herein, particularly nucleic acids containing the HCRTR1 gene described herein. For instance, a nucleotide or nucleic acid construct (vector) comprising a nucleotide of the present invention can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other agents.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The agents are administered in a therapeutically effective amount. The amount of agents which will be therapeutically effective in the treatment of narcolepsy can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

METHODS OF THERAPY

The present invention also pertains to methods of therapy for narcolepsy, utilizing the pharmaceutical compositions comprising nucleic acids, as described herein. The therapy is designed to replace/supplement activity of the hypocretin (orexin) receptor 1 in an individual, such as by administering a nucleic acid comprising the HCRTR1 gene or a derivative or active fragment thereof. In one embodiment of the invention, a nucleic acid of the invention is used in the treatment of narcolepsy. The term, "treatment" as used herein, refers not only to ameliorating symptoms associated with the disease, but also preventing or delaying the onset of the disease, and also lessening the severity or frequency of symptoms of the disease. In this embodiment, a nucleic acid of the invention (e.g., the HCRTR1 gene (SEQ ID NO:1)) can be used, either alone or in a pharmaceutical composition as described above. For example, the HCRTR1 gene, either by itself or included within a vector, can be introduced into cells (either in vitro or in vivo) such that the cells produce native HCRTR1 receptor. If necessary, cells that have been transformed with the gene or can be introduced (or re-introduced) into an individual affected with the disease. Thus, cells which, in nature, lack native HCRTR1 expression and activity, or have mutant HCRTR1 expression and activity, can be engineered to express HCRTR1 receptors (or, for example, an active fragment of the HCRTR1 receptor). In a preferred embodiment, nucleic acid comprising the HCRTR1 gene, can be introduced into an expression vector, such as a viral vector, and the vector can be introduced into appropriate cells which lack native HCRTR1 expression in an animal. In such methods, a cell population can be engineered to inducibly or constitutively express active HCRTR1 receptor. Other gene transfer systems, including viral and nonviral transfer systems, can be used. Alternatively, nonviral gene transfer methods, such as calcium phosphate coprecipitation, mechanical techniques (e.g., microinjection); membrane fusion-mediated transfer via liposomes; or direct DNA uptake, can also be used.

The nucleic acids and/or vectors are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount which will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patients circumstances. Effective doses may be extrapolated from dose-response curves derived from in vitro or animal model test systems.

The following Examples are offered for the purpose of illustrating the present invention and are not to be construed to limit the scope of this invention. The teachings of all references cited herein are hereby incorporated herein by reference.

EXAMPLES

Example 1

Identification of the Human Narcolepsy Gene

A human BAC library (RPCI11 human male BAC library) was used. Seventeen primers, designed from the mRNA sequence of the HCRTR1 receptor, were employed to identify clones of interest. They are set forth in Table 1.

TABLE 1

Primers Used for Hybridization

| Number | Name | Primer Sequence | SEQ ID NO: |
|---|---|---|---|
| 1 | HCRTR1-1-F | TCAGGAAGTTTGAGGCTGAGA | 3 |
| 2 | HCRTR1-1-R | ATCCTAGGCTCTACAGAGGGA | 4 |
| 3 | HCRTR1-2-F | GAAGATGAGTTTCTCCGCTATC | 5 |
| 4 | HCRTR1-2-R | GATGAGGACCCACTCATACTG | 6 |
| 5 | HCRTR1-3-F | ACATGAGGACAGTCACCAACTA | 7 |
| 6 | HCRTR1-3-R | CAGATAGCAGTCACCAGAACG | 8 |
| 7 | HCRTR1-4-F | ACATCACTGAGTCCTGGCTGT | 9 |
| 8 | HCRTR1-4-R | ATGAAGCTGAGAGTTAGCACTG | 10 |
| 9 | HCRTR1-5-F | CTATTGTTCAAGAGCACAGCC | 11 |
| 10 | HCRTR1-5-R | CATCACAGACTGAGAAGAGCC | 12 |

TABLE 1-continued

Primers Used for Hybridization

| Number | Name | Primer Sequence | SEQ ID NO: |
|---|---|---|---|
| 11 | HCRTR1-6-R | CTTCACTTCAGCCAGGAAGG | 13 |
| 12 | HCRTR1-7-F | AATGTCCTTAAGAGGGTGTTCG | 14 |
| 13 | HCRTR1-7-R | GAAGTTGTAGATGATGGGGTTG | 15 |
| 14 | HCRTR1-8-F | CACAAGTCCTTGTCCTTGCAG | 16 |
| 15 | HCRTR1-8-R | CACCACATGCTCAGAGATTTTG | 17 |
| 16 | HCRTR1-9-F | CCTACCCCTCATGGAAAGAC | 18 |
| 17 | HCRTR1-9-R | ATCCAGAGTCACACAGGCAGA | 19 |

Initial Study with Large Membranes

Four out of 5 membranes having the whole BAC library, containing a total of approximately 160,000 BAC clones representing an approximately 10-fold coverage of the human genome, were used in hybridization studies with these primers. Hybridization was performed with a pool of all 17 primers described in Table 1.

5' End Labeling for Big Membranes

Oligonucleotides were labeled at the 5' end before hybridization, using fresh [$\gamma^{32}$P]ATP (6000 Ci/mmole; 10 µCi/µl). Briefly, a labeling mixture was made of DNA (8 pmol/µl) (10.0 µl of the primer pool), 10×buffer (12.0 µl), T4 PNK (10 u/µl) (6.0 µl), [$\gamma^{32}$P]ATP (30.0 µl, or 600 µCi), and water (62.0 µl) for a final volume of 120 µl. 20 µl of labeling mixture was used per 10 ml rapid hybridization reaction. Incubation of the labeling mixture was for 2 hours at 37° C., followed by transfer to ice, spinning down, and mixing with the rapid hybridization solution. The membranes were pre-hybridized at 42° C. before the labeling mix was added. Sixty µl of the labeling mix was added to each of 2 big bottles containing 2 membranes and 30 ml of rapid hybridization solution.

Hybridization and Washing

The membranes were hybridized at 42° C. overnight. After overnight, membranes were washed with 6×SSC, 0.1% SDS at room temperature; washed with 6×SSC, 0.1% SDS at 55° C. in a shaking waterbath, repeated until the radioactivity of membranes was lower than 6 k using 1× sensitivity; and washed with 6×SSC to remove the SDS. The washed membranes were put in a cassette for overnight exposure at −80° C. with a MR single emulsion film. Positive clones were identified and gridded on small membranes.

Study of Positive Clones with Small Membranes

After growing the positively-identified clones on several small membranes (to get several copies of membranes containing the same clones), and washing the membranes, hybridization was performed using pairs of primers, instead of a total pool of primers as before. The total number of hybridizations was nine, using different primers against identical copies of membranes containing all positive clones from the first hybridization. The primer pairs are set forth in Table 2; primer numbers indicate the primers shown in Table 1.

TABLE 2

Primer Pairs Used for Hybridization

| Reaction number | Primers Used |
|---|---|
| 1 | 1 and 2 |
| 2 | 3 and 4 |
| 3 | 5 and 6 |
| 4 | 7 and 8 |
| 5 | 9 and 10 |
| 6 | 11 |
| 7 | 12 and 13 |
| 8 | 14 and 15 |
| 9 | 16 and 17 |

5' End Labeling for Small Membranes

Oligonucleotides were labeled at the 5' end before hybridization, using fresh [$\gamma^{32}$P]ATP (5000 Ci/mmole; 10 µCi/µl). Briefly, a labeling mixture was made of DNA (8 pmol/µl) (1.5 µl), 10×buffer (2.0 µl), T4 PNK (10 u/µl) (1.0 µl), [$\gamma^{32}$P]ATP (3.0 µl), and water (12.5 µl) for a final volume of 20 µl. Incubation of the labeling mixture was for 2.5 hours at 37° C., followed by transfer to ice, spinning down, and mixing with the rapid hybridization solution. Membranes were pre-wetted in 6×SSC, rolled in a pipette, and excess liquid drained prior to placing the membrane in the tube. Fifty ml Falcon (polypropylene) tubes were used as container for the hybridization. The membranes were prehybridized at 42° C. before 20 µl of labeling mix was added to each tube.

Hybridization and Washing

The membranes were hybridized at 42° C. overnight. After overnight, membranes were washed as described above. Four clones which were positive for primers designed using the 5' and 3' end of the mRNA were identified. Clone 333N1 was used to characterize the gene.

Sequencing of Narcolepsy Gene in Clone 33N1

Shotgun sequencing, supplemented with sequencing of PCR products amplified from 333N1, was used to obtain the gene sequence.

Shotgun Sequencing

Preparation of DNA Samples

BAC DNA was isolated using the Plasmix kit from TALENT-VH Bio Limited. Thirty µg of isolated DNA was fragmented by nebulization: a nebulizer (IPI Medical Products, Inc., no. 4207) was modified by removing the plastic cylinder drip ring, cutting off the outer rim of the cylinder, inverting it and placing it back into the nebulizer; the large hole in the top cover (where the mouth piece was attached) was sealed with a plastic stopper, the small hole was connected to a ¼ inch length of Tycon tubing (connected to a compressed air source). A DNA sample was prepared containing 30 µg DNA, 10×TM buffer (200 µl), sterile glycerol (1 ml), and sterile dd water (q.s.) for a total volume of 2 ml. The DNA sample was nebulized in an ice-water bath for 2 minutes and 40 seconds (pressure bar reading 0.5). The sample was then briefly centrifuged at 2500 rpm to collect the DNA; the entire unit was placed in the rotor bucked of a table top centrifuge (Beckman GPR tabletop centrifuge) fitted with pieces of Styrofoam to cushion the nebulizer. The sample was then distributed into four 1.5 ml microcentrifuge tubes and ethanol precipitated. The Dried DNA pellet was resuspended in 35 µl of 1×TM buffer prior to proceeding with fragment end-repair.

Fragment End Repair, Size Selection and Phosphorylation

The DNA was resuspended in 27 µl of 1×TM buffer. The following materials were added: 10×kinase buffer (5 µl), 10 mM rATP (5 µl), 0.25 mM dNTPs (7 µl), T4 polynucleotide kinase (1 µl (3 U/µl)), Klenow DNA polymerase (2 µl (5

U/μl)), T4 DNA polymerase (1 μl (3 U/μl)), for a total volume of 48 μl. The mixture was incubated at 37° C. for 30 minutes, and then 5 μl of agarose gel loading dye was added. The mixture was then applied to separate wells of a 1% low melting temperature agarose gel and electrophoresed for 30–60 minutes at 100–120 mA. The DNA was then eluted from each sample lane, extracted from the agarose using Ultrafree-DA columns (Millipore) and then cleaned with Microcon-100 columns (Amicon), precipitated in ethanol, and resuspended in 10 μl of 10:0.1 TE buffer.

Ligation

EcoRV-linearized, CIAP-dephosphorylated Bluescript vector was used as a cloning vector. The following reagents were combined in a microcentrifuge tube, and incubated overnight at 4° C.: DNA fragments (100–1000 ng), cloning vector (2 μl (10 ng/μl)), 10×ligation buffer (1 μl), T4 DNA ligase (NEB 202L) (1 μl (400 U/μl)), sterile dd water (q.s.), for a total of 10 μl.

Transformation of Ligated Products

The ligation products were diluted 1:5 with dd water and used to transform electrocompetent TOP 10F cells (Invitrogen) using GenePulser II (Biorad; voltage, 2.5 W, resistance 100 ohm). Transformants were plated on LB plates with 50 μl of 4% X-GAL and 50 μl of 4% IPTG, and ampicillin. Transformants were grown overnight at 37° C., white colonies were picked, grown in a culture of 3 ml LB liquid media plus 200 μg/μl ampicillin for 16–20 hours with shaking. DNA was isolated from the liquid cultures using Autogen 740 Automatic Plasmid Isolation System.

Cycle Sequencing of Isolated Plasmid DNA

Isolated plasmids were then sequenced using the M13 primers: M13-forward (SEQ ID NO:20) TGTAAAAC-GACGGCCAG; and M13-reverse (SEQ ID NO:21) CAG-GAAACAGCTATGAC. For the sequencing reaction, 2.5 μl plasmid template was mixed with 4 μl Big Dye Ready reaction mix (ABI), 1 μl of 8 pM M13 primer, and 2.5 μl dd water. For cycle sequencing, 25 cycles of 96° C. for 10 seconds, 50° C. for 5 seconds, and 60° C. for 4 minutes were performed, followed by holding at 4° C. The cycle sequencing reaction products were cleaned by spinning through Sephadex G-50 columns. The eluted cycle sequencing products were then dissolved in 3 μl formamide/dye and 1.5 μl of sample was loaded on ABI 377 automated sequencers. The data was analyzed using Phred and Phrap, and viewed in Consed viewer.

PCR Product Sequencing

In order to supplement the sequencing described above, PCR products of BAC 33N1 were also sequenced. Primers used for the hybridizations, as described above, were used to amplify regions of 333N1 by long PCR using GeneAmpXL PCR kit (Perkin Elmer). The sequence for HCRTR1-6F is as follows:

TCTTTATTGTCACCTACCTGGC (SEQ ID NO:22).

TABLE 3

PCR Product Sequencing Pairs

| Primer Pair Used for PCR | Primers Used for Cycle Sequencing of PCR Product |
|---|---|
| HCRTR1-1F/HCRTR1-4R | HCRTR1-1F,2F,3F,4F,1R,2R,3R,4R |
| HCRTR1-1F/HCRTR1-6R | HCRTR1-1F,2F,3F,5F,6F,1R,2R,3R |
| HCRTR1-4F/HCRTR1-7R | HCRTR1-4F,5F,6F,7F,4R,5R,6R,7R |
| HCRTR1-6F/HCRTR1-8R | HCRTR1-6F,6R,7R,8R |
| HCRTR1-7F/HCRTR1-9R | HCRTR1-7F,8F,7R,8R,9R |

The PCR products were prepared for cycle sequencing by incubation at 37° C. for 15 minutes and then at 87° C. for 15 minutes to destroy the enzymes. The PCR products were then subject to cycle sequencing as described above, with the same procedures for sequencing gel runs and sequence analysis.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated nucleic acid molecule comprising the nucleic acid of SEQ ID NO:1.

2. A DNA construct comprising the isolated nucleic acid molecule of claim 1 operatively linked to a regulatory sequence.

3. A recombinant host cell comprising the isolated nucleic acid molecule of claim 1 operatively linked to a regulatory sequence.

* * * * *